(12) United States Patent
Sluijterman et al.

(10) Patent No.: US 9,208,993 B2
(45) Date of Patent: Dec. 8, 2015

(54) CHARGED-PARTICLE MICROSCOPY WITH ENHANCED ELECTRON DETECTION

(71) Applicant: FEI Company, Hillsboro, OR (US)

(72) Inventors: Albertus Aemillius Seyno Sluijterman, Eindhoven (NL); Eric Gerardus Theodoor Bosch, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/558,334

(22) Filed: Dec. 2, 2014

(65) Prior Publication Data

US 2015/0155131 A1    Jun. 4, 2015

(30) Foreign Application Priority Data

Dec. 2, 2013    (EP) .................................... 13195289

(51) Int. Cl.
*H01J 37/26* (2006.01)
*H01J 37/244* (2006.01)

(52) U.S. Cl.
CPC .............. *H01J 37/244* (2013.01); *H01J 37/26* (2013.01); *H01J 37/265* (2013.01); *H01J 2237/153* (2013.01); *H01J 2237/221* (2013.01); *H01J 2237/2441* (2013.01)

(58) Field of Classification Search
USPC ............. 250/396 R, 397, 305, 306, 307, 309, 250/310, 311
See application file for complete search history.

(56) References Cited

U.S. PATENT DOCUMENTS

2004/0188611 A1* 9/2004 Takeuchi et al. .............. 250/310
2005/0134181 A1   6/2005 Jang et al.

(Continued)

FOREIGN PATENT DOCUMENTS

EP    2665083      11/2013
EP    2665083 A2   11/2013

(Continued)

OTHER PUBLICATIONS

Sznitman, Raphael, et al. "Efficient Scanning for EM Based Target Localization," Medical Image Computing and Computer-Assisted Intervention, 2012, pp. 337-344.

(Continued)

*Primary Examiner* — Nicole Ippolito
(74) *Attorney, Agent, or Firm* — Scheinberg & Associates, PC; Michael O. Scheinberg (57) ABSTRACT

A method of investigating a flux of output electrons emanating from a sample in a charged-particle microscope, which flux is produced in response to irradiation of the sample by a beam of input charged particles, the method comprising the following steps:

Using a detector to intercept at least a portion of the flux so as to produce a set $\{I_j\}$ of pixeled images $I_j$ of at least part of the sample, whereby the cardinality of the set $\{I_j\}$ is M>1.

For each pixel p, in each image $I_j$, determining the accumulated signal strength $S_{ij}$, thus producing an associated set of signal strengths $\{S_{ij}\}$.

Using the set $\{S_{ij}\}$ to calculate the following values:
An average signal strength S per pixel position i;
A variance $\sigma^2_S$ in S per pixel position i.

Using these values S and $\sigma^2_S$ to at least one map of said part of the sample, selected from the group comprising:
A first map, representing variation in energy of detected electrons as a function of position.
A second map, representing variation in number of detected electrons as a function of position.

The set $\{I_j\}$ may be produced in different ways, such as:
By iteratively repeating a procedure whereby an entire $n^{th}$ image $I_n$ is captured before proceeding to capture an entire $(n+1)^{th}$ image $I_{n+1}$, or
By iteratively repeating a procedure whereby, at an $n^{th}$ pixel position, a plurality M of different detector samples is collected before proceeding to an $(n+1)^{th}$ pixel position.

20 Claims, 4 Drawing Sheets

(56) References Cited

U.S. PATENT DOCUMENTS

2008/0251718 A1* 10/2008 Kaga et al. .................. 250/310
2012/0032078 A1* 2/2012 Stekelenburg et al. ....... 250/307
2013/0054153 A1 2/2013 Motl et al.

FOREIGN PATENT DOCUMENTS

| JP | 2005134181 | 5/2005 |
|---|---|---|
| WO | 00/70646 | 11/2000 |
| WO | 0070646 | 11/2000 |
| WO | 03/003402 | 1/2003 |
| WO | 03003402 A1 | 1/2003 |
| WO | 2006/109564 | 10/2006 |
| WO | 2006019564 A1 | 10/2006 |
| WO | 2009/079195 | 6/2009 |
| WO | 2009079195 A1 | 6/2009 |

OTHER PUBLICATIONS

Sznitman, Raphael, et al., "Efficient Scanning for EM Based Target Localization", Medical Image Computing and Computer-Assisted Intervention Miccai, 2012, Berlin, Heidelberg, pp. 337-344.

* cited by examiner

CHARGED-PARTICLE MICROSCOPY WITH ENHANCED ELECTRON DETECTION

The invention relates to a method of investigating a flux of output electrons emanating from a sample in a charged-particle microscope, which flux is produced in response to irradiation of the sample by a beam of input charged particles.

The invention additionally relates to a charged-particle microscope comprising:
- A charged-particle source, for producing an irradiating beam of charged particles.
- A sample holder, for holding a sample to be irradiated.
- A particle-optical column, for directing said beam onto said sample.
- A detector, for detecting a flux of output electrons emanating from the sample in response to said irradiation.

As used throughout this text, the ensuing terms should be interpreted consistent with the following explanation:

The phrase "charged particle" encompasses an electron or ion (generally a positive ion, such as a Gallium ion or Helium ion, for example, although a negative ion is also possible; the ion in question may be a charged atom or molecule). The term may also refer to a proton, for example.

The term "microscope" refers to an apparatus that is used to create a magnified image of an object, feature or component that is generally too small to be seen in satisfactory detail with the naked human eye. In a charged-particle microscope (CPM), a beam of input charged particles is directed onto a sample using a so-called "particle-optical column", which comprises a collection of electrostatic and/or magnetic lenses that can be used to manipulate said beam, serving to provide it with a certain focus or deflection, for example, and/or to mitigate one or more aberrations therein. In certain types of CPM, a different particle-optical column may also be used to focus charged particles emanating from the sample onto a detector. In addition to imaging, a CPM may also have other functionalities, such as performing spectroscopy, examining diffractograms, performing (localized) surface modification (e.g. milling, etching, deposition), etc. In what follows, the invention will—by way of example—often be set forth in the specific context of electron microscopes. However, such simplification is intended solely for clarity/illustrative purposes, and should not be interpreted as limiting.

Charged-particle microscopy is a well-known and increasingly important technique for imaging microscopic objects, particularly in the form of electron microscopy. Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various subspecies, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example. In a TEM, the electron beam used to irradiate a sample will generally be of significantly higher energy than in the case of a SEM (e.g. 300 keV vs. 10 keV), so as to allow its constituent electrons to penetrate the full depth of the sample; for related reasons, a sample investigated in a TEM will also generally need to be thinner than one investigated in a SEM. In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example.

When a charged-particle beam impinges on a sample, it generally interacts with the sample in a manner that causes different types of output radiation to emanate from the sample. Such output radiation may, for example, comprise electrons (including so-called Secondary Electrons and/or Backscattered Electrons), visible/infrared/ultraviolet light (fluorescence and cathodoluminescence) and X-rays. Of these radiation types:

- Electrons may, for example, be detected using a photomultiplier tube (PMT) in conjunction with a scintillator. It should be noted in this context that the employed PMT may be based on an evacuated vitreous tube containing dynodes, or may instead employ a solid-state semiconductor-based detection element (as in the case of a so-called Multi-Pixel Photon Counter (MPPC®)/Solid State Photo-Multiplier (SSPM)). One may also, for example, use a photodiode cell, Charge-Coupled Device (CCD) or Complementary Metal Oxide Semiconductor (CMOS) detector, possibly supplemented by a scintillator.
- Photonic radiation in the form of visible/infrared/ultraviolet light can, for example, be detected using a PMT (without scintillator), a photodiode cell, a CCD or a CMOS detector.
- X-rays tend to be more difficult to detect. Detectors for this purpose are typically relatively expensive and slow, and generally offer a relatively limited field of view. However, X-ray detection is conventionally of great use in performing compositional/elemental analyses of samples, such as in the case of so-called EDS (Energy Dispersive X-ray Spectroscopy) detectors, for example The current invention is concerned with the first of these types of output radiation, i.e. electrons. In many uses of a CPM, Backscattered (BS) electrons tend to play a more important role than Secondary Electrons, and this document may here and there make some explicit reference to BS electrons in this context; however, this should not be interpreted as limiting for the scope of application of the current invention and claims. In addition, in the case of a TEM (or STEM), the input beam of electrons (substantially) passes through the sample and emerges as a transmitted beam of output electrons, which proceeds to an analyzing device such as a fluorescent screen, imaging camera, EELS module, etc. (EELS=Electron Energy-Loss Spectrometry); in principle, the present invention can also be used to analyze such transmitted electrons. Inter alia in the context of the elucidation just given, reference is made to the following explanatory Wikipedia links, for general information purposes:

http://en.wikipedia.org/wiki/Secondary_electrons
http://en.wikipedia.org/wiki/Scanning_electron_microscope (sections concerning detection of Secondary and Backscattered electrons).
http://en.wikipedia.org/wiki/Transmission_electron_microscopy The imaging of a sample using an electron flux emanating therefrom exploits the fact that, for given input beam parameters, the number and/or energy of electrons emerging from a given point on the sample will be influenced by the structure and/or composition of the sample at the point in question. Recording and visually rendering the flux value as a function of position on the sample can thus be used to create an "image" of the sample (or at least a part thereof). A problem with this procedure, however, is that the electron generation and detection processes involved are intrinsically "convoluted", inter alia as a result of the following:

The electron generation process is statistical in nature, in that there is generally temporal variability in the numbers and/or energies of electrons emanating from a given point on the sample (for a given stimulation using an input beam).

Conventional electron detection in a CPM involves the registering of cumulative electron energy during a given temporal window (after which a refresh/reset will occur). In this context, a typical detector will, for example, not be able to discern whether a registered cumulative energy was due to a low flux of high-energy electrons, or a high flux of low-energy electrons, or a hybrid/mixed scenario.

Consequently, an electron-based image of a sample in a CPM is intrinsically "jumbled" as regards its information content.

It is an object of the invention to address the issues raised above. More specifically, it is an object of the invention to provide a method as set forth in the opening paragraph above, whereby an acquired electron image of the sample can be (at least partially) deconvolved. In particular, it is an object of the current invention that such a method should allow more specific electron imaging of a sample to be performed.

These and other objects are achieved in a method as set forth in the opening paragraph above, which method is characterized in that it comprises the following steps:

Using a detector to intercept at least a portion of the flux so as to produce a set $\{I_j\}$ of pixeled images of at least part of the sample, whereby the cardinality of the set $\{I_j\}$ is M>1.

For each pixel pi in each image Ij, determining the accumulated signal strength Sij, thus producing an associated set of signal strengths $\{S_{ij}\}$.

Using the set $\{S_{ij}\}$ to calculate the following values:
An average signal strength S per pixel position i;
A variance $\sigma^2_S$ in S per pixel position i.

Using these values S and σ2S to produce at least one map of said part of the sample, selected from the group comprising:
A first map, representing variation in energy of detected electrons as a function of position;
A second map, representing variation in number of detected electrons as a function of position.

As regards the terminology used here, it should be noted that:
An image Ij is considered to be "pixeled" if it can be sub-divided into a plurality of (real or imaginary) constitutive sub-regions—which may or may not correspond to detection pixels in a case where a pixelated detector is used to produce the image in question.

Each/either of said first and second maps is produced using both of the values of S and σ2S.

The skilled artisan will fully grasp these points.

The current invention exploits the insight that the statistical nature of the electron emission process set forth above can be exploited advantageously rather than being regarded as a nuisance. The inventors took the unusual step of recording multiple images of a sample—not for conventional noise reduction purposes, but to act purely as a basis to perform statistical analysis. This might generally be considered as counter-productive, e.g. in terms of throughput penalty and generally increased radiation dose to the sample. However, by examining these various images on a pixel-by-pixel basis, and mathematically processing them, the fact that the inventors had recorded multiple (temporally disparate) images allowed statistical averages/means (S) and variances ($\sigma^2_S$) per pixel to be distilled from the data. This effectively amounted to a deconvolution process, whereby two different parameters could be separated from one another in data that was initially "muddled" in nature. By considering the electron production/imaging process in more detail, the inventors realized that the distilled values of S and $\sigma^2_S$ scaled in different ways with the energy (E) and number (N) of electrons arriving at the detector, thus allowing a separate "E-map" and "N-map" of the sample to be produced. This can, for example, be explained as follows:

The quantity S demonstrates functional behavior that can be expressed as follows:

$$S \sim EN_o \eta \quad (1)$$

whereby:

$N_o$ describes the average number of charged particles (e.g. electrons) in the input beam, and demonstrates variations according to a Poisson process.

η describes the probability of detecting a signal at the employed detector, and demonstrates variations according to a binomial process.

E describes the average energy of the detected electrons resulting from the impact of a single input particle, and varies according to an unknown random process.

The combination of said Poisson and binomial processes results in a Poisson process with an average value $N=N_o\eta$, being a measure of the number of detected electrons per input particle. One can thus write:

$$S \sim EN \quad (1a)$$

The variance $\sigma^2_S$ in S demonstrates functional behavior that can be expressed as follows:

$$\sigma^2_S \sim E^2 N \quad (2)$$

Combining expressions (1a) and (2), it follows that:

$$E = f(S, \sigma^2_S) \quad (3)$$

$$N = g(S^2, \sigma^2_S) \quad (4)$$

where f and g are functions. For example:

$$E \sim \sigma^2_S / S \quad (3a)$$

$$N \sim S^2 / \sigma^2_S \quad (4a)$$

Since these values are calculated per pixel, a plot of their values per pixel respectively renders:

A first map (E-map) of the sample, which essentially reveals only compositional variation across the (imaged part of the) sample (e.g. regions comprising different contaminants/dopants, general transitions from one material to another, etc.);

A second map (N-map) of the sample, which inter alia reveals topographical variation across the (imaged part of the) sample (e.g. edges, bumps and hollows, trenches and ridges, granulation, cracking, etc.).

One can thus separate two different types of information from the same imagery, rather than having to put up with some forced hybrid/mix of the two. The ability to distill out the first map (E-map) is particularly interesting, because it gives rudimentary compositional information without having to resort to X-ray spectroscopy (EDS).

The skilled artisan will be well able to quantify S and $\sigma^2_S$ from analysis of the set $\{S_{ij}\}$, e.g. using relatively straightforward software to automatically analyze the data $\{S_{ij}\}$ and determine attendant averaged amplitudes and spreads per pixel. In so doing, he has the freedom to choose from various estimators for the required average/mean and variance; for example, in the case of the quantify S, the employed average/mean may be a simple arithmetic average (sum of values divided by number of values), or another type of estimator. Similarly, relatively simple software will be able to automatically perform calculations such as those set forth in equations (3a) and (4a) above, for example. The software in question may be executed with the aid of a controller, such as an electronic microprocessor, which may also be programmed/invoked to automatically collect the dataset $\{I_j\}$, render the first and second maps on a display device, etc. Inter alia in the context of the elucidation just given, reference is made to the following explanatory Wikipedia links, for general information purposes:

http://en.wikipedia.org/wiki/Average
http://en.wikipedia.org/wiki/Variance
http://en.wikipedia.org/wiki/Standard_deviation Needless to say, the accuracy of the procedure set forth in the previous paragraph will depend inter alia on the number M of accumulated images $I_j$, i.e. on the cardinality M of the set $\{I_j\}$. This is a matter of choice, and the skilled artisan will be able to decide how to manage the tradeoff between greater accuracy (in the calculated values of S and $\sigma_S$) on the one hand, and the competing issue of throughput on the other hand. Another issue that may need to be considered is the total radiation dose delivered to the sample, and an acceptable upper limit in this regard may place a restriction on the value of M. However, the inventors have observed that, because the current invention is predominantly interested in the differences between images in the set $\{I_j\}$ more than on the direct content of the images themselves, there are situations in which it is possible to lower the dose per image so as to (partially) compensate for the multiplicity of images acquired thus decreasing the cumulative radiation dose for the whole image set $\{I_j\}$. Moreover, in calculating values of S and $\sigma^2_S$ from analysis of the set $\{S_{ij}\}$, intelligent algorithms can be used to produce more refined values of S and $\sigma^2_S$ from smaller data sets, e.g. by extrapolating/interpolating data from a cluster of ancillary (neighboring) pixels adjacent to any given subject pixel; in this way, one can suffice with a smaller value of M to start off with. By way of non-limiting example, provided for general guidance purposes only, the inventors achieved satisfactory results with the current invention in the case of a sample comprising gold islands on carbon and using M in the range 50-300, for instance.

For purposes of information and guidance, a supplemental elucidation of (some of) the considerations in the previous paragraph can be set forth as follows. Considering the detection of BS electrons, and taking E and N to be specified by equations (3a) and (4a), respectively, one can derive the following (somewhat simplified) expressions for the relative errors in E and N, with respective standard deviations $\sigma_E$ and $\sigma_N$:

$$\frac{\sigma_E}{E} \sim \sqrt{\frac{1}{NM\gamma} + \frac{2}{M-1} + \frac{\kappa}{M}} \quad (5)$$

$$\frac{\sigma_N}{N} \sim \sqrt{\frac{4}{NM\gamma} + \frac{2}{M-1} + \frac{\kappa}{M}} \quad (6)$$

in which:

$$\gamma = \frac{E^2}{E^2 + \sigma_E^2} \quad (7)$$

$$N = N_o \eta \quad (8)$$

where:
As already alluded to above, $N_o$ is the dose per image, $\eta$ is the BS electron yield combined with the detector yield, and M is the cardinality of the set $\{I_j\}$.
$\kappa$ is the so-called Kurtosis of distribution of the measured signal in question, with $\kappa \sim 1/N$ (e.g. $\kappa \approx 22/N$ for carbon and $\kappa \approx 2/N$ for gold).

On the basis of such relationships, the skilled artisan can play off M and N against one another, for given desired/acceptable values of $\sigma_E/E$ and $\sigma_N/N$. In so doing, he may, for simplicity, set $\gamma \approx 1$, for example.

Inter alia in the context of the elucidation just given, reference is made to the following explanatory Wikipedia link, for general information purposes:
http://en.wikipedia.org/wiki/Kurtosis It should be noted that, according to the current invention, there are different manners in which the set $\{I_j\}$ can be produced. For example:
(i) In one approach, the set $\{I_j\}$ is produced by iteratively repeating (with a total of M iterations) a procedure in which an entire $n^{th}$ image $I_n$ is captured before proceeding to capture an entire $(n+1)^{th}$ image $I_{n+1}$. In this case, the set $\{I_j\}$ is basically a stack of M individual pre-assembled images $I_j$.
Such an approach can, for example, be enacted using detection scheme (a) or (b) below.
(ii) In an alternative approach, the set $\{I_j\}$ is produced by iteratively repeating a procedure in which, at an $n^{th}$ pixel position, a plurality M of different detector samples is collected before proceeding to an $(n+1)^{th}$ pixel position. In this case, the set $\{I_j\}$ is basically assembled by juxtaposing pixel stacks on a two-dimensional floor area—somewhat like mini-skyscrapers with M floors arranged side-by-side; a given image $I_n$ is then the cumulative floor area made up of all $n^{th}$ floors of the individual skyscrapers in question. So, in this case, individual images can be regarded as post-assembled rather than pre-assembled. In this scenario, whether or not one actually takes the trouble to explicitly "resolve" (assemble) individual images $I_j$ out of the "unresolved" set $\{I_j\}$ is not of particular relevance to the current invention: the main object is to accrue the dataset $\{S_{ij}\}$ and the associated values of S and $\sigma^2_S$ via the set $\{I_j\}$ (resolved or not). Such an approach can, for example, be enacted using detection scheme (a) below.
(iii) If desired, one can conceive various hybrids/mixes of approaches (i) and (ii).

As regards the detection schemes alluded to above, the following possibilities can be considered:
(a) Scan-based detection, whereby:
The detector is a single-segment detector (for example);
An image is produced by scanning the beam of input charged particles relative to the sample.
In this scenario, a narrow beam of input charged particles irradiates only a small region of the sample at any given time, and the employed detector intercepts (a portion of) the flux of electrons emerging from the irradiated region in question, so as to create a component image sub-section. This process is repeated at successive regions on the sample (following a scan path), and a full image can then be assembled by "tiling" the obtained component image sub-sections together. This is the procedure commonly employed in a SEM, for example.

(b) "Full-field" detection. Here, the full sample (or a relatively large area thereof) is irradiated using a relatively broad beam of input charged particles, and a pixelated detector (such as a CCD or CMOS array, for example) is used to capture electrons emanating from the whole irradiated zone on the sample, leading to outright formation of a two-dimensional image. Such a procedure is commonly employed in a TEM, for example.

(c) If desired, one can conceive various hybrids/mixes of schemes (a) and (b).

The skilled artisan will be able to grasp these points and choose for himself the manner in which he wishes to accumulate the set $\{S_{ij}\}$ via the set $\{I_j\}$.

In a particular embodiment of the current invention, the flux of output electrons comprises BS electrons. BS electrons lend themselves particularly to application of the statistical processing approach of the present invention because they tend to have a relatively large energy spread. Moreover, they tend to yield better detection contrast than secondary electrons, for example. In addition, the relatively high energy of BS electrons (as compared to secondary electrons) makes them relatively easy to detect vis-à-vis the typical detection threshold of commonly employed detectors.

Another embodiment of the present invention is characterized in that the employed detector is a solid state detector. Solid state detectors have certain advantages over more conventional dynode-based PMTs. For example, the former have good linearity in detected energy, and tend to be (much) smaller and cheaper than the latter. In addition, the former can, if desired, be relatively easily embodied as integrated pixelated detectors, which is not possible for the latter. In the context of such solid state detectors, the inventors have achieved particularly good results for the current invention with detectors that employ boron-doped detection cells (such as a delta-doped boron $p^+$ n photodiode, for example). Such boron-doped detectors are advantageous inter alia in that they are relatively sensitive and highly linear, even for electron energies as low as ca. 200 eV. As regards the basic structure and operation of such detectors, more information can, for example, be gleaned from the following technical journal links:

http://ectm.et.tudelft.nl/publications_pdf/document1249.pdf
http://www.electrochem.org/dl/ma/202/pdfs/0672.PDF

BRIEF DESCRIPTION OF THE DRAWINGS

The invention will now be elucidated in more detail on the basis of exemplary embodiments and the accompanying schematic drawings, in which.

In the Figures, where pertinent, corresponding parts are indicated using corresponding reference symbols. It should be noted that, in general, the Figures are not to scale.

DETAILED DESCRIPTION OF EXAMPLE EMBODIMENTS

Embodiment 1

Figure 1:
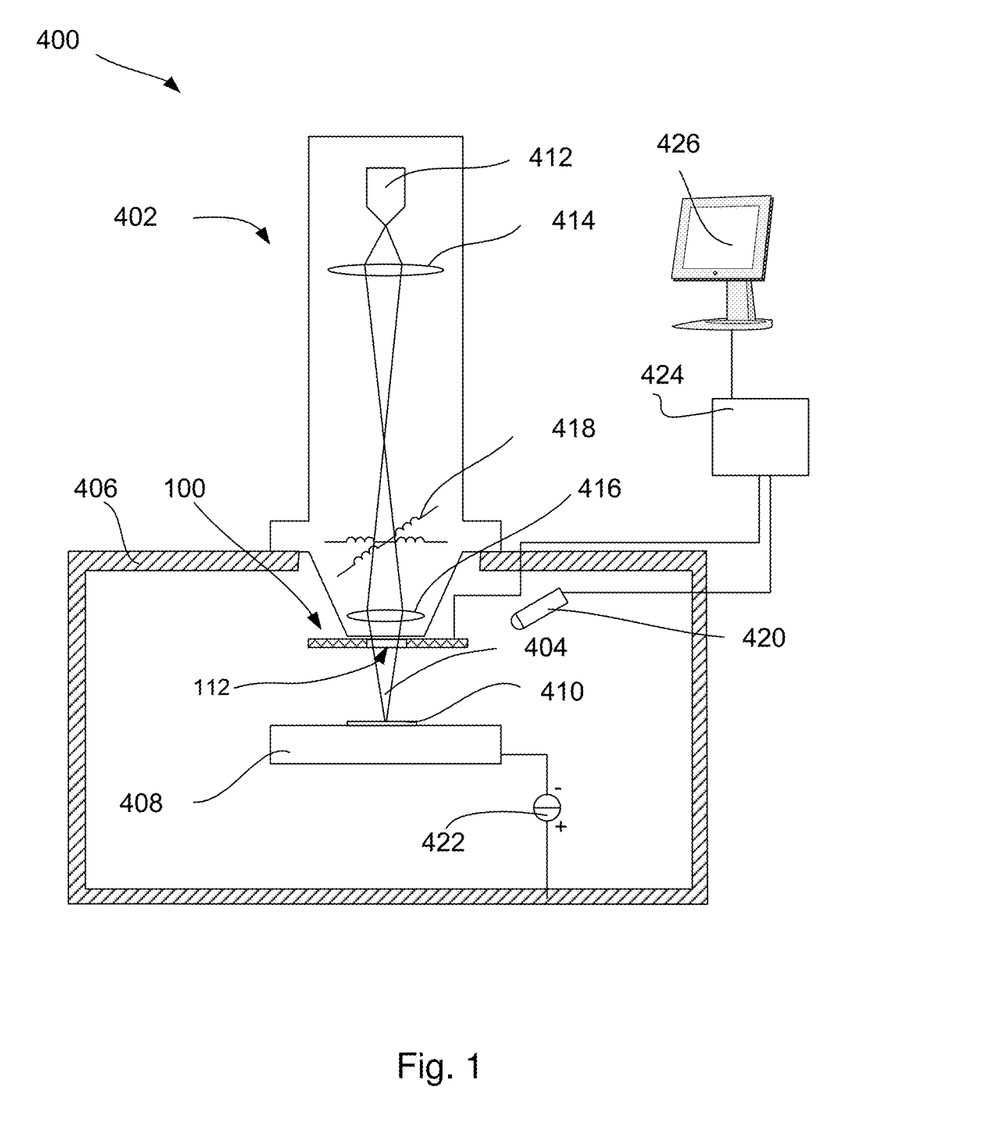
FIG. 1 renders an elevational view of a charged-particle microscope that lends itself to use with the current invention.

FIG. 1 is a highly schematic depiction of a charged-particle microscope 400, which, in this case, is a SEM. The microscope 400 comprises a particle-optical column 402, which produces a beam 404 of input charged particles (in this case, an electron beam). The particle-optical column 402 is mounted on a vacuum chamber 406, which comprises a sample holder/stage 408 for holding a sample 410. The vacuum chamber 406 is evacuated using vacuum pumps (not depicted). With the aid of voltage source 422, the sample holder 408, or at least the sample 410, may, if desired, be biased (floated) to an electrical potential with respect to ground.

The particle-optical column 402 comprises an electron source 412 (such as a Schottky gun), lenses 414, 416 to focus the electron beam 404 onto the sample 410, and a deflection unit 418 (to perform beam steering/scanning of the beam 404). The apparatus 400 further comprises a controller/computer processing apparatus 424 for controlling inter alia the deflection unit 418, lenses 414, 416 and detectors 100, 420, and displaying information gathered from the detectors 100, 420 on a display unit 426.

The detectors 420, 100 are chosen from a variety of possible detector types that can be used to examine different types of output radiation emanating from the sample 410 in response to irradiation by the input beam 404. In the apparatus depicted here, the following detector choices have been made:

Detector 100 is a segmented electron detector. Such a detector can, for example, be used to investigate the angular dependence of a flux of output (secondary) electrons emerging from the sample 410.

Detector 420 is a boron-doped solid state detector that is used to detect (at least a portion of) a flux of output BS electrons emanating from the sample 410.

As here rendered, both detectors 100 and 420 are used to examine electrons; however, this is purely a design/implementation choice and, if desired, one could also elect to detect other types of output radiation emanating from the sample 410 (e.g. X-rays, cathodoluminescence) in addition to electrons.

By scanning the input beam 404 over the sample 410, output radiation comprising, for example, X-rays, infrared/visible/ultraviolet light, secondary electrons and backscattered (BS) electrons—emanates from the sample 410. As such output radiation is position-sensitive (due to said scanning motion), the information obtained from the detectors 100, 420, will also be position-dependent. This fact allows the output of detector 420 to be used to produce a BS electron image of (part of) the sample 410, which image is basically a map of an output of detector 420 as a function of scan-path position on the sample 410.

The signals from the detectors 100, 420 are processed by the controller 424, and displayed on display unit 426. Such processing may include operations such as combining, integrating, subtracting, false colouring, edge enhancing, and other processing known to the skilled artisan. In addition, automated recognition processes (e.g. as used for particle analysis) may be included in such processing. In the specific context of the current invention, the controller 424—and/or a dedicated separate processing unit (not shown)—can be used to perform the following actions:

Using detector 420 to produce a set $\{I_j\}$ of pixeled BS electron images $I_j$ of at least part of the sample 410, whereby the cardinality of the set $\{I_j\}$ is M>1. As set forth above, this may, for example be done:

On a pixel-by-pixel basis, whereby M samples of the BS electron flux are measured in succession at a given position on the sample 410 before moving the beam 404 onto a next position on the sample 410; or On an image-by-image basis, whereby an entire scan of (said part of) the sample 410 is made by beam 404, leading to creation of a whole image $I_j$, and this procedure is performed a total of M times in succession.

For each pixel pi in each image Ij, determining the accumulated signal strength Sij, thus producing an associated set of signal strengths {Sij}.

Using the set {Sij} to calculate the following values:
An average signal strength S per pixel position i;
A variance σ2S in S per pixel position i.

Using these values S and σ2S (as input to equations (3a) and (4a) above, for example), to produce one or both of the following maps of said part of the sample 410:

A first map, representing variation in energy (E) of detected BS electrons as a function of position on the sample 410.

A second map, representing variation in number (N) of detected BS electrons as a function of position on the sample 410.

Figure 2A:
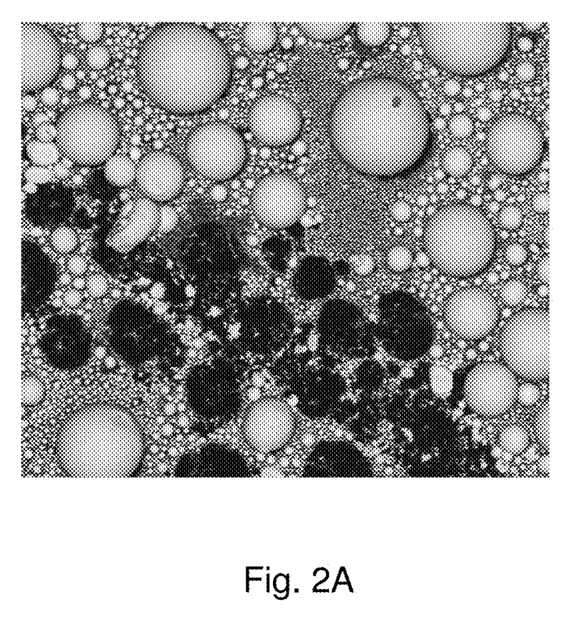
FIG. 2A shows a conventional BS electron image of part of a tin-on-carbon sample.
Figure 2B:
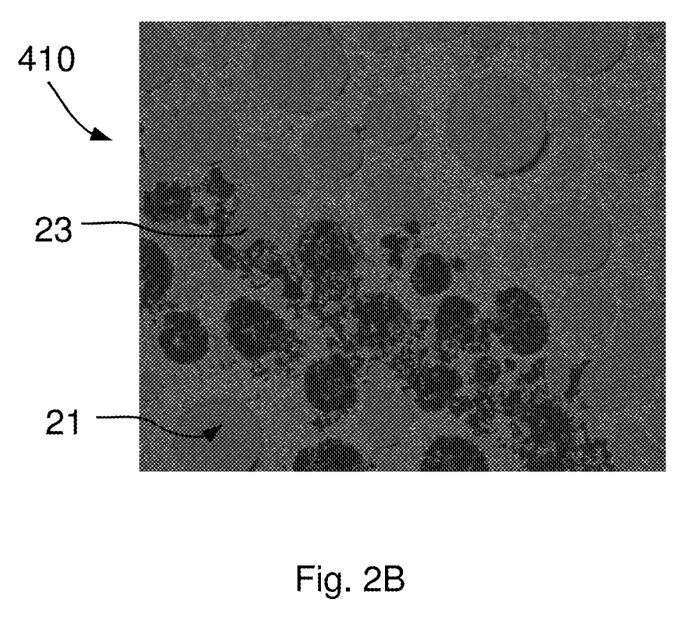
FIG. 2B shows the subject of FIG. 2A, but now rendered as a first-type map (E-map) using the current invention, and revealing compositional information.
Figure 2C:
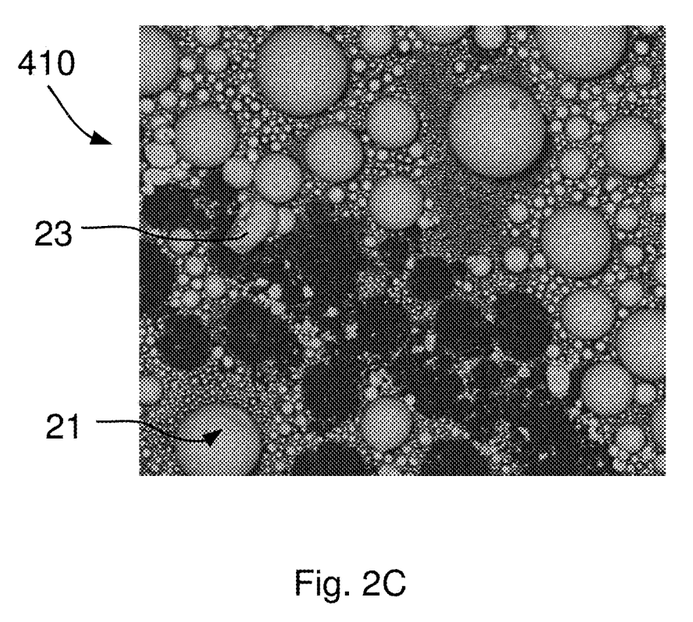
FIG. 2C also shows the subject of FIG. 2A, but now rendered as a second-type map (N-map) using the current invention, and inter alia revealing (mainly) topographical information.

Examples of E- and N-maps produced by the invention in this manner are illustrated in FIGS. 2B and 2C below, respectively.

It should be noted that many refinements and alternatives of such a set-up will be known to the skilled artisan, including, but not limited to:

The use of dual beams—for example an electron beam 404 for imaging and an ion beam for machining (or, in some cases, imaging) the sample 410;

The use of a controlled environment at the sample 410— for example, maintaining a pressure of several mbar (as used in a so-called Environmental SEM) or by admitting gases, such as etching or precursor gases, etc.

For more information on some of the topics alluded to above, reference is made to the following Wikipedia links:
http://en.wikipedia.org/wiki/Field_emission_gun
http://en.wikipedia.org/wiki/Electron_optics Embodiment 2

FIGS. 2A, 2B and 2C illustrate the effect of a particular embodiment of the current invention as enacted using a set-up as set forth in Embodiment 1 above. The figures all show part of the same sample 410, which in this case comprises tin (Sn) droplets sputtered on carbon (C), imaged using BS electrons in a SEM on the basis of the following imaging parameters:

Landing energy of input electron beam 404: 5 keV.
Beam current of input electron beam 404: 170 pA.
Dwelling time τ=6 μs (=time to compile a single pixel of the BS electron image).
M (cardinality of measured image set {Ij})=300, i.e. 300 different BS electron measurement samples were recorded per pixel position, or 300 full BS electron images Ij were serially acquired.

Each of the figures shows an image with lateral dimensions of ca. 50 μm×42 μm.

FIG. 2A shows a conventional BS electron image of part of the employed sample 410, being an averaged image derived from the set $\{I_j\}$. As already explained above, this image is convoluted/unresolved as regards the energies (E) and numbers (N) of BS electrons triggering the detection events used to assemble the image. However, by processing the set $\{I_j\}$ to produce a set $\{S_{ij}\}$ as set forth above in accordance with the current invention, the image in FIG. 2A can be deconvolved/resolved into a pair of separate maps. In this context:

FIG. 2B shows the subject of FIG. 2A, but now rendered using the current invention as a first-type map (E-map) as alluded to above, and revealing compositional information of the employed sample 410. The contrast-to-noise ratio (CNR) for the depicted map is ca. 3.56.

FIG. 2C also shows the subject of FIG. 2A, but now rendered using the current invention as a second-type map (N-map) as alluded to above, and revealing inter alia (mostly) topographical information of the employed sample 410.

Comparing FIGS. 2B and 2C to FIG. 2A, it is, for example, seen that:

An oval "dent" 21 visible in FIG. 2C is absent from FIG. 2B.

A droplet 23 that appears to be substantially wrinkled/broken in FIG. 2C appears substantially featureless in FIG. 2B.

Such differences are consistent with the fact that the E-map in FIG. 2B renders compositional information rather than topographical information.

Embodiment 3

Figure 3:
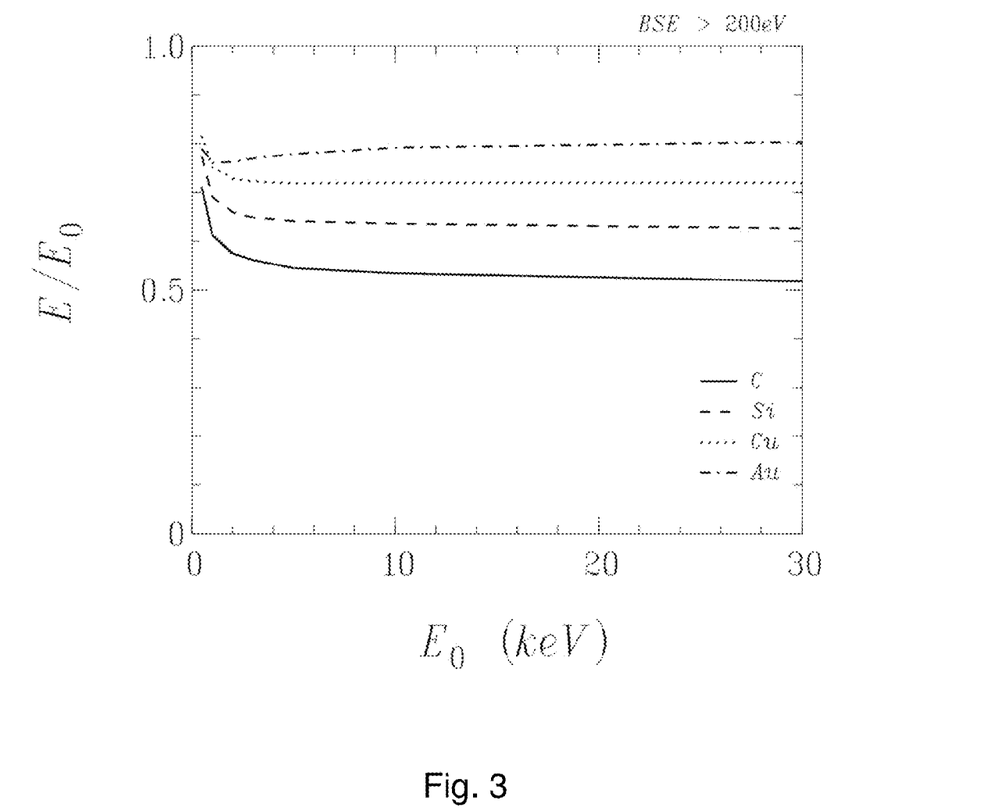
FIG. 3 graphically illustrates how the energy of BS electrons emitted from a test sample depends on the elemental constitution of that sample.

FIG. 3 graphically illustrates how the energy of BS electrons emitted from a test sample depends on the elemental constitution of that sample. The graph plots detected BS electron energy E (normalized to the landing energy $E_o$ of the input beam) as a function of said landing energy $E_o$, for test samples comprising pure Au, Cu, Si and C. The fact that the plotted E-curves are clearly separated from one another over most of their extent (above about $E_o \approx 1$ keV) illustrates the type of composition-dependent contrast that underlies the concept of an E-map as referred to above.

We claim as follows:

1. A method of investigating a flux of output electrons emanating from a sample in a charged-particle microscope, which flux is produced in response to irradiation of the sample by a beam of input charged particles, the method comprising the following steps:

using a detector to intercept at least a portion of the flux so as to produce a set $\{I_j\}$ of pixeled images $I_j$ of at least part of the sample, whereby the cardinality of the set $\{I_j\}$ is M>1;

for each pixel pi in each image $I_j$, determining the accumulated signal strength Sij, thus producing an associated set of signal strengths $\{S_{ij}\}$;

using the set $\{S_{ij}\}$ to calculate the following values:
an average signal strength S per pixel position i;
a variance $\sigma^2_S$ in S per pixel position i;

using these values S and $\sigma^2_S$ to produce at least one map of said part of the sample, selected from the group comprising:
a first map, representing variation in energy of detected electrons as a function of position, and;
a second map, representing variation in number of detected electrons as a function of position.

2. A method as claimed in claim 1, wherein the set $\{I_j\}$ is produced by iteratively repeating a procedure whereby an entire $n^{th}$ image In is captured before proceeding to capture an entire $(n+1)^{th}$ image $I_{n+1}$.

3. A method as claimed in claim 1, wherein the set $\{I_j\}$ is produced by iteratively repeating a procedure whereby, at an $n^{th}$ pixel position, a plurality M of different detector samples is collected before proceeding to an $(n+1)^{th}$ pixel position.

4. A method according to claim 1, wherein said flux of output electrons comprises backscattered electrons.

5. A method according to claim 1, wherein said detector is a solid state detector.

6. A method according to claim 5, wherein said solid state detector comprises at least one boron-doped diode detection cell.

7. A method according to claim 1, wherein said first map is produced with the aid of a functional dependence $E \sim \sigma_S^2/S$ per pixel position i.

8. A method according to claim 1, wherein said second map is produced with the aid of a functional dependence $N \sim S^2/\sigma_S^2$ per pixel position i.

9. A charged-particle microscope comprising:
- a charged-particle source, for producing an irradiating beam of charged particles;
- a sample holder, for holding a sample to be irradiated;
- a particle-optical column, for directing said beam onto said sample;
- a detector, for detecting a flux of output electrons emanating from the sample in response to said irradiation; and
- a controller programmed to perform the following actions:
- using said detector to produce a set $\{I_j\}$ of pixeled images $I_j$ of at least part of the sample, whereby the cardinality of the set $\{I_j\}$ is M>1;
- for each pixel $p_i$ in each image $I_j$, determining the accumulated signal strength $S_{ij}$, thus producing an associated set of signal strengths $\{S_{ij}\}$;
- using the set $\{S_{ij}\}$ to calculate the following values:
  - an average signal strength S per pixel position i;
  - a variance $\sigma^2_S$ in S per pixel position i;
- using these values S and $\sigma^2_S$ to produce at least one map of said part of the sample, selected from the group comprising:
  - a first map, representing variation in energy of detected electrons as a function of position;
  - a second map, representing variation in number of detected electrons as a function of position.

10. The charged particle microscope of claim 9, wherein the controller is programmed to produce the set $\{I_j\}$ by iteratively repeating a procedure whereby an entire $n^{th}$ image is captured before proceeding to capture an entire $(n+1)^{th}$ image $I_{n+1}$.

11. The charged particle microscope of claim 9, wherein the controller is programmed to produce the set $\{I_j\}$ by iteratively repeating a procedure whereby, at an $n^{th}$ pixel position, a plurality M of different detector samples is collected before proceeding to an $(n+1)^{th}$ pixel position.

12. The charged particle microscope of claim 9, wherein said flux of output electrons comprises backscattered electrons.

13. The charged particle microscope of claim 9, wherein said first map is produced with the aid of a functional dependence $E \sim \sigma_S^2/S$ per pixel position i.

14. The charged particle microscope of claim 9, wherein said second map is produced with the aid of a functional dependence $N \sim S^2/\sigma_S^2$ per pixel position i.

15. A method of generating pixeled maps of a sample comprising:
- irradiating a sample by a beam of input charged particles sample in a charged-particle microscope;
- measuring the flux of output electrons emanating from a sample in the charged-particle microscope, which flux is produced in response to irradiation of the sample by a beam of input charged particles; and
- generating at least one of a first pixeled map of the sample using the variation in energy of electrons arriving at a detector and a second pixeled map of the sample using the number of electrons arriving at a detector.

16. The method of claim 15 wherein the first map is generated with the aid of a functional dependence $E \sim \sigma_S^2/S$ per pixel position i.

17. The method of claim 15 wherein the second map is generated with the aid of a functional dependence $N \sim S^2/\sigma_S^2$ per pixel position i.

18. The method of claim 15 wherein the output electrons are backscattered electrons.

19. The method of claim 15, wherein the detector is a solid-state detector.

20. The method of claim 19, wherein said solid state detector comprises at least one boron-doped diode detection cell.

* * * * *